(12) United States Patent
Nogueiras Nieto et al.

(10) Patent No.: US 11,911,509 B2
(45) Date of Patent: Feb. 27, 2024

(54) PHARMACEUTICAL COMPOSITION COMPRISING LENVATINIB MESYLATE

(71) Applicant: Synthon B.V., Nijmegen (NL)

(72) Inventors: Luis Nogueiras Nieto, Sant Boi de Llobregat (ES); Lisardo Alvarez Fernandez, Sant Boi de Llobregat (ES); Jose Velada Calzada, Nijmegen (NL); Rohit Kumar, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 600 days.

(21) Appl. No.: 16/603,031

(22) PCT Filed: Apr. 4, 2018

(86) PCT No.: PCT/EP2018/058629
§ 371 (c)(1),
(2) Date: Oct. 4, 2019

(87) PCT Pub. No.: WO2018/185175
PCT Pub. Date: Oct. 11, 2018

(65) Prior Publication Data
US 2020/0188380 A1 Jun. 18, 2020

(30) Foreign Application Priority Data
Apr. 4, 2017 (EP) ..................... 17164761

(51) Int. Cl.
*A61K 31/47* (2006.01)
*A61K 47/02* (2006.01)
*A61K 47/26* (2006.01)
*A61K 47/38* (2006.01)
*A61K 9/16* (2006.01)
*A61K 9/00* (2006.01)

(52) U.S. Cl.
CPC .......... *A61K 9/1694* (2013.01); *A61K 9/0046* (2013.01); *A61K 31/47* (2013.01); *A61K 47/02* (2013.01); *A61K 47/26* (2013.01); *A61K 47/38* (2013.01)

(58) Field of Classification Search
CPC .... A61K 9/1694; A61K 9/0046; A61K 31/47; A61K 47/02; A61K 47/26; A61K 47/38; A61K 9/1611; A61K 9/1623; A61K 9/1652; A61K 9/485; A61K 9/4866; A61K 9/0007
See application file for complete search history.

(56) References Cited

U.S. PATENT DOCUMENTS

2008/0131503 A1* 6/2008 Holm ............... A61K 45/06
424/463
2012/0077842 A1 3/2012 Bando

FOREIGN PATENT DOCUMENTS

| EP | 1415987 A1 | 5/2004 |
| EP | 1797881 A1 | 6/2007 |
| EP | 2468281 A1 | 6/2012 |

(Continued)

*Primary Examiner* — Savitha M Rao
*Assistant Examiner* — Andrew P Lee
(74) *Attorney, Agent, or Firm* — Buscher Patent PLLC

(57) ABSTRACT

The present invention relates to a pharmaceutical composition comprising a therapeutically effective dose of Lenvatinib mesylate having sodium wherein the weight ratio of Lenvatinib mesylate to sodium carbonates ranges from 1:1.5 to 1:5.

17 Claims, 1 Drawing Sheet

(56) References Cited

FOREIGN PATENT DOCUMENTS

WO    WO-2017028660 A1 *   2/2017  ............. A61K 31/47
WO    WO 2017028860 A1     2/2017

* cited by examiner

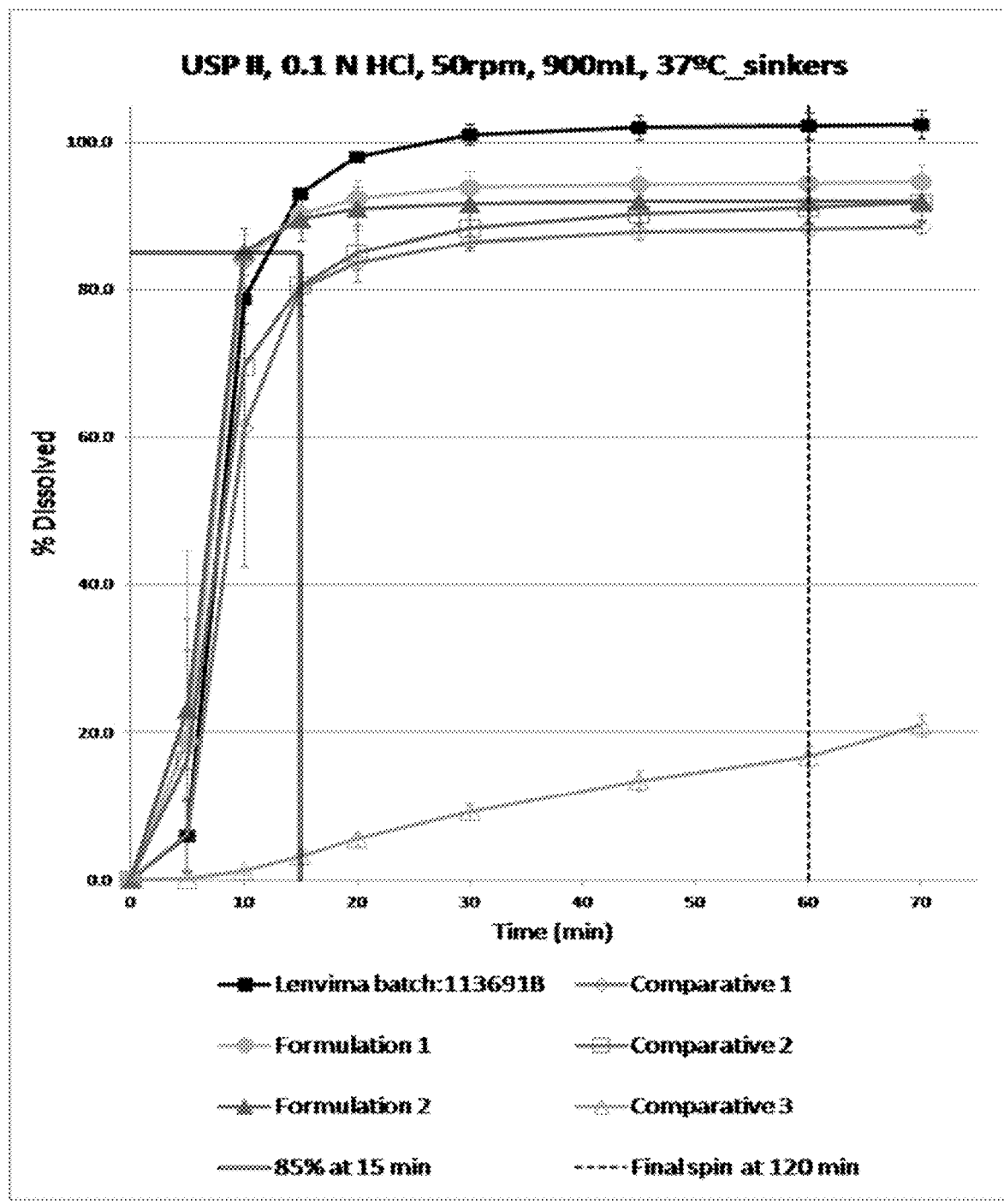

PHARMACEUTICAL COMPOSITION COMPRISING LENVATINIB MESYLATE

BACKGROUND OF THE PRESENT INVENTION

The present invention relates to a pharmaceutical composition, comprising Lenvatinib mesylate, having improved bioavailability.

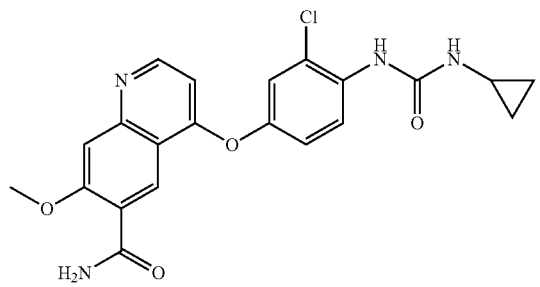 [SMILES: COc1cc2nccc(Oc3ccc(NC(=O)NC4CC4)c(Cl)c3)c2cc1C(N)=O]

Lenvatinib having the chemical structure shown above is an angiogenesis and C-Kit kinase inhibitor, and as such it is used as a therapeutic agent against various tumors such as thyroid cancer, lung cancer, melanoma and pancreatic cancer.

Lenvatinib and pharmaceutically acceptable salts thereof are disclosed in European Patent application EP1415987.

Lenvatinib mesylate degrades under humidifying and warm storage conditions when formulated into a pharmaceutical composition. Furthermore, it is known that Lenvatinib mesylate gelifies when in contact with dissolution media, this may cause a delay in its release. EP1797881 discloses a pharmaceutical composition that solved the above problems using an alkaline excipient with a pH of 8 a 5% w/w aqueous solution to reduce the degradation of the active substance and silicic acid to inhibit gelation. Sodium carbonates are described as suitable alkaline excipient.

EP2468281 discloses that when an alkaline earth metal carbonate is used as a base in combination with a disintegrant the pharmaceutical compositions have superior dissolution properties than other bases, even after long term storage. During prosecution the applicant provided results showing that when non earth metal carbonates such as sodium bicarbonate were used as stabilizers, the dissolution rate decreased after storage as compared to before storage and the dissolution time was additionally delayed.

There is still need of finding additional oral formulation of Lenvatinib mesylate which overcome the problems of gelation and degradation and is bioequivalent to the commercial Lenvatinib mesylate capsules (Lenvima®).

DETAILED DESCRIPTION OF THE PRESENT INVENTION

The present invention relates to a pharmaceutical composition comprising a therapeutically effective dose of Lenvatinib mesylate and sodium carbonates wherein the weight ratio of Lenvatinib mesylate to sodium carbonates ranges from 1:1.5 to 1:5, most preferred ranges are from 1:2 to 1:4.

Sodium carbonates within this invention encompass sodium carbonate ($Na_2CO_3$), sodium bicarbonate ($NaHCO_3$), or mixtures of both, for instance effersoda which is sodium bicarbonate coated with sodium carbonate. A preferred carbonate within the invention is sodium bicarbonate.

The inventors have found that surprisingly, formulations comprising Lenvatinib mesylate and sodium carbonates, wherein the weight ratio of lenvatinib mesylate to sodium carbonates ranges from 1:1.5 to 1:5 are stable and are bioequivalent to the commercial Lenvatinib mesylate capsules (Lenvima®).

In the acidic environment of the gastrointestinal tract, sodium carbonates produce $CO_2$:

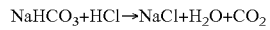

$$NaHCO_3 + HCl \rightarrow NaCl + H_2O + CO_2$$

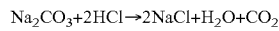

$$Na_2CO_3 + 2HCl \rightarrow 2NaCl + H_2O + CO_2$$

The $CO_2$ produced has a disintegrant effect that allows Lenvatinib mesylate to disperse in very small fine particles avoiding gelation. The alkaline nature of the sodium carbonates prevents degradation and reduces impurity formation, including genotoxic impurities that may be formed upon hydrolysation of Lenvatinib mesylate. Moreover, the inventors have found that surprisingly, when the sodium carbonates are used in the ratio of the invention, the stability and the disintegration properties of these carbonates are such that Lenvatinib mesylate can be formulated without the addition of an extra disintegrant, as described in EP2468281. The addition of an extra disintegrant is optional and the skill person could decide to add it.

Furthermore, sodium carbonates and specially $NaHCO_3$, have better solubility in water than the earth metal carbonates described in EP2468281 improving the pharmaceutical processability i.e. wet granulation with water.

The processability is improved in such a way that no binder is needed in such formulations. The addition of an extra binder is optional.

In one embodiment, the present invention relates to a pharmaceutical composition comprising a therapeutically effective dose of Lenvatinib mesylate having a particle size distribution $D_{90}$ from 5 to 50 μm, preferably from 8 to 25 μm, most preferred from 10 to 15 μm.

The $D_{90}$ value of the particle size distribution is defined as the particle diameter at which 90% by volume of the particles have a smaller diameter than the diameter which corresponds to the $D_{90}$ value measured by laser diffractometry. Specifically, a Malvern Instruments Mastersizer was used to determine the particle size distribution.

Besides sodium carbonates one or more pharmaceutically acceptable excipients can be used additionally in accordance with the present invention.

In a preferred embodiment sodium carbonates are used in an amount of 14% to 65%, preferably 20% to 55%, more preferably 20% to 50%, most preferably 25% to 50% by weight based on the total weight of the composition.

The one or more pharmaceutically acceptable excipients to be used additionally to sodium carbonates in accordance with the present invention can be chosen from, for example, diluents, binders, disintegrants, lubricants, and glidants.

Diluents are fillers which are used to increase the bulk volume of a tablet or capsule. By combining a diluent with the active pharmaceutical ingredient, the final product is given adequate weight and size to assist in production and handling. Binders hold the excipients that are present in a tablet/granule together.

The pharmaceutical composition of the present invention preferably contains at least one diluent.

Diluents are preferably used in an amount of from 15% to 75%, preferably 30% to 70%, more preferably 35% to 65%, even more preferably 35% to 55% by weight based on the total weight of the composition. Suitable examples of diluents to be used in accordance with the present invention include starch, pregelatinized starch, microcrystalline cellulose (MCC), mannitol, and calcium phosphate.

In a preferred embodiment of the present invention, the diluents to be used are mannitol, microcrystalline cellulose or mixtures thereof.

The pharmaceutical composition of the present invention may also contain a binder. Binders ensure that tablets and granules can be formed having the desired or required mechanical strength. Binders which are suitable for use in accordance with the present invention include povidone, hydroxypropyl cellulose, hydroxypropyl methylcellulose, and sodium carboxyl methylcellulose. Binders are preferably used in an amount of from 1% to 6% by weight based on the total weight of the composition.

The pharmaceutical composition of the present invention may also contain an extra disintegrant. Disintegrants are added to a tablet or capsule composition to promote the breakup of the tablet/capsule into smaller fragments in an aqueous environment, thereby increasing the available surface area and promoting a more rapid release of the active pharmaceutical ingredient. Suitable examples of disintegrants to be used in accordance with the present invention include crospovidone, L-HPC (Low substituted hydroxypropyl cellulose), sodium starch glycolate, croscarmellose sodium, and mixtures of any of the foregoing. Extra disintegrants preferably are used in an amount of from 1% to 25% by weight based on the total weight of the composition; the amount will depend on the tablet size and the chosen disintegrant. A preferred extra disintegrant is low substituted hydroxypropyl cellulose, in a preferred amount of from 15% to 25% by weight based on the total weight of the composition.

The pharmaceutical composition of the invention may also contain a lubricant. Lubricants are generally used in order to reduce sliding friction. In particular, to decrease the friction at the interface between the blend to be encapsulated and dosator of the encapsulation machine. Suitable lubricants to be used in accordance with the present invention include magnesium stearate, stearic acid, glyceryl behenate, hydrogenated vegetable oil, talc and glycerine fumarate. A preferred lubricant is talc. The pharmaceutical composition of the invention may also contain a glidant. Glidants enhance product flow by reducing interparticulate friction. A suitable example is colloidal silicon dioxide.

Lubricants and glidants preferably are used in a total amount of from 0.05% to 5% by weight based on the total weight of the composition.

In a preferred embodiment, the pharmaceutical composition of the present invention, wherein the weight ratio of Lenvatinib mesylate to sodium carbonates ranges from 1:1.5 to 1:5, contains the following ingredients, based on the total weight of the composition:
   a. A therapeutically effective dose of Lenvatinib mesylate in an amount of from 4% to 30% by weight, preferably 4% to 25% by weight;
   b. Microcrystalline cellulose in an amount of from 10% to 65% by weight, 20% to 65% by weight, more preferably 25% to 55% by weight, even more preferably 27% to 45% by weight;
   c. Sodium carbonates, preferably sodium hydrogen carbonate, from 20% to 55% by weight, preferably from 20 to 50% by weight, more preferably 25 to 50% by weight;
   d. Optionally, Low substituted hydroxypropyl cellulose in an amount of from 15-25% by weight.
   e. Mannitol in an amount of from 7% to 18% by weight, preferably 5% to 10% by weight; and
   f. From 1% to 5% by weight of a lubricant and a glidants, preferably talc.

In one embodiment of the present invention, the therapeutically effective dose of Lenvatinib is 4 mg, 10 mg, 18 mg and 24 mg.

The compositions of the present invention can be prepared by direct mixing or granulating the Lenvatinib mesylate with one or more pharmaceutically acceptable excipients, optionally followed by encapsulation, using equipment and methods well-known to the skilled artisan.

In a preferred embodiment the composition are prepared by granulation process. Granulation can be performed by a wet or dry process, wherein wet granulation using water or organic solvents or mixtures thereof as granulation liquid and dry granulation can be performed by processes known as slugging and/or roller compaction.

The pharmaceutically acceptable excipients to be used in accordance with the present invention, can be used only intragranularly, only extragranularly, or both.

In a preferred embodiment the granules of the present invention are prepared by a wet-granulation process comprising the steps:
   1. Mixing Lenvatinib mesylate, sodium carbonates, preferably $NaHCO_3$, wherein the weight ratio of Lenvatinib mesylate to sodium carbonates ranges from 1:1.5 to 1:5 most preferred ranges are from 1:2 to 1:4.
   2. Wet-granulating the resulting mixture;
   3. Further mixing the obtained granulate with one or more further pharmaceutically acceptable excipients to form a further mixture;
   4. Optionally encapsulating the granules The granules of the present invention typically have a particle size distribution $D_{50}$ of from 200-350 μm, more preferably from 250 to 300 μm.

The present invention also relates to a pharmaceutical composition comprising granulates as described hereinabove in the form of a capsule or a tablet, preferably a capsule.

The pharmaceutical compositions described herein can be made using conventional methods and equipment well-known in the art.

The pharmaceutical compositions of the present invention show an in vitro dissolution profile wherein at least 80% of Lenvatinib mesylate is released at fifteen minutes when the composition is subjected to a dissolution study in 900 ml HCl 0.1N (pH 1) using a USP apparatus II at 50 rpm at 37° C. Preferably, at least 85% of Lenvatinib mesylate is released from the pharmaceutical composition at fifteen minutes. The pharmaceutical composition in accordance with the present invention is bioequivalent to the commercially available Lenvatinib mesylate capsules.

BRIEF DESCRIPTION OF THE DRAWING

The sole FIGURE shows the in vitro dissolution profile of capsule compositions in accordance with the present invention (formulations A and B) and comparatives examples 1, 2 and 3, as compared to commercially available capsules of Lenvatinib mesylate (Lenvima® 10 mg).

The present invention is illustrated by the following Examples.

EXAMPLES

Example 1

TABLE 1

Pharmaceutical composition of formulation A.
Formulation A

| Components | mg/capsule | % |
|---|---|---|
| Intragranular | | |
| Lenvatinib mesylate | 12.25 | 12.25% |
| Sodium hydrogen carbonate | 33.00 | 33.00% |
| Mannitol | 8.75 | 8.75% |
| Microcrystalline cellulose | 21.50 | 21.50% |
| Extragranular | | |
| Microcrystalline cellulose | 21.50 | 21.50% |
| Talc | 3.00 | 3.00% |
| Total weight | 100.00 | 100.00% |

3.68 grams of lenvatinib mesylate, 9.90 grams of sodium hydrogen carbonate, 2.63 grams of mannitol and 6.45 grams of microcrystalline cellulose were weighted and sieved through a 0.8 mm mesh for the deagglomeration of the materials. Afterwards, the mentioned components were mixed for 5 minutes in a vessel at 150 rpm by means of an IKA Eurostard stirrer. Then 9 grams of distilled water was added to the blend in the vessel mixing the components at 150 rpm using the former stirrer. The wetted granules obtained were sieved through 2.8 mm mesh and placed in a oven at 40° C. under vacuum conditions for 24 hours. The loss on drying of the granules was measured by means of a halogen moisture analyzer. Once the final granules were dried (1), 6.45 grams of microcrystalline cellulose were weighted and sieved through 0.8 mesh and then mixed with the obtained granules (1) for 10 minutes at 72 rpm resulting in a homogenous blend (2). 0.90 grams of talc were weighted and sieved through 0.5 mm and then mixed with the previous blend (2) for 3 minutes at 72 rpm resulting in a homogenous blend (3). The resulting blend (3) was then encapsulated into hypromellose hard capsules size 4.

Example 2

TABLE 2

Pharmaceutical composition of formulation B.
Formulation B

| Components | mg/capsule | % |
|---|---|---|
| Lenvatinib mesylate | 12.25 | 12.25% |
| Sodium hydrogen carbonate | 33.00 | 33.00% |
| Mannitol | 8.75 | 8.75% |
| Microcrystalline cellulose | 43.00 | 43.00% |
| Talc | 3.00 | 3.00% |
| Total weight | 100.00 | 100.00% |

3.68 grams of lenvatinib mesylate, 9.90 grams of sodium hydrogen carbonate, 2.63 grams of mannitol and 12.90 grams of microcrystalline cellulose were weighted and sieved through a 0.8 mm mesh for the deagglomeration of the materials and then mixed for 10 minutes at 72 rpm resulting in a homogenous blend (1). 0.90 grams of talc were weighted and sieved through 0.5 mm and then mixed with the previous blend (1) for 3 minutes at 72 rpm resulting in a homogenous blend (2). The resulting blend (2) was then encapsulated into hypromellose hard capsules size 4.

Example 3

TABLE 3

Pharmaceutical composition of formulation C.
Formulation B

| Components | mg/capsule | % |
|---|---|---|
| Lenvatinib mesylate | 12.25 | 9.80% |
| Sodium hydrogen carbonate | 41.25 | 33.00% |
| Mannitol | 20.125 | 16.10% |
| Microcrystalline cellulose | 22.5 | 18.00% |
| Low substituted hydroxypropyl cellulose | 25.125 | 20.10% |
| Talc | 3.75 | 3.00% |
| Total weight | 125.00 | 100.00% |

8.33 grams of lenvatinib mesylate, 28.05 grams of sodium hydrogen carbonate, 13.69 grams of mannitol, 15.30 grams of microcrystalline cellulose and 17.09 grams of low substituted hydroxypropyl cellulose were weighted and sieved through a 0.8 mm mesh for the deagglomeration of the materials and then mixed for 10 minutes at 72 rpm resulting in a homogenous blend (1). 2.55 grams of talc were weighted and sieved through 0.5 mm and then mixed with the previous blend (1) for 3 minutes at 72 rpm resulting in a homogenous blend (2). The resulting blend (2) was then encapsulated into hypromellose hard capsules size 4.

Comparative Example 1

| Components | mg/capsule | % |
|---|---|---|
| Lenvatinib mesylate | 12.25 | 12.25% |
| Sodium hydrogen carbonate | 76 | 76% |
| Mannitol | 8.75 | 8.75% |
| Talc | 3.00 | 3.00% |
| Total weight | 100.00 | 100.00% |

2.45 grams of lenvatinib mesylate, 15.20 grams of sodium hydrogen carbonate, 1.75 grams of mannitol were weighted and sieved through a 0.8 mm mesh for the deagglomeration of the materials and then mixed for 10 minutes at 72 rpm resulting in a homogenous blend (1). 0.6 grams of talc were weighted and sieved through 0.5 mm and then mixed with the previous blend (1) for 3 minutes at 72 rpm resulting in a homogenous blend (2). The resulting blend (2) was then encapsulated into hypromellose hard capsules size 4.

Comparative Example 2

| Components | mg/capsule | % |
|---|---|---|
| Lenvatinib mesylate | 12.25 | 12.25% |
| Sodium hydrogen carbonate | 12.25 | 12.25% |
| Mannitol | 8.75 | 8.75% |
| Microcrystalline cellulose | 63.75 | 63.75% |
| Talc | 3.00 | 3.00% |
| Total weight | 100.00 | 100.00% |

3.06 grams of lenvatinib mesylate, 3.06 grams of sodium hydrogen carbonate, 2.19 grams of mannitol and 15.94 grams of microcrystalline cellulose were weighted and sieved through a 0.8 mm mesh for the deagglomeration of the materials and then mixed for 10 minutes at 72 rpm resulting in a homogenous blend (1). 0.75 grams of talc were weighted and sieved through 0.5 mm and then mixed with the previous blend (1) for 3 minutes at 72 rpm resulting in a homogenous blend (2). The resulting blend (2) was then encapsulated into hypromellose hard capsules size 4.

Comparative Example 3

| Components | mg/capsule | % |
|---|---|---|
| Lenvatinib mesylate | 12.25 | 12.25% |
| Microcrystalline cellulose | 76 | 76% |
| Mannitol | 8.75 | 8.75% |
| Talc | 3.00 | 3.00% |
| Total weight | 100.00 | 100.00% |

2.45 grams of lenvatinib mesylate, 15.20 grams of microcrystalline cellulose, 1.75 grams of mannitol were weighted and sieved through a 0.8 mm mesh for the deagglomeration of the materials and then mixed for 10 minutes at 72 rpm resulting in a homogenous blend (1). 0.6 grams of talc were weighted and sieved through 0.5 mm and then mixed with the previous blend (1) for 3 minutes at 72 rpm resulting in a homogenous blend (2). The resulting blend (2) was then encapsulated into hypromellose hard capsules size 4.

The invention claimed is:

1. A pharmaceutical composition comprising (i) a therapeutically effective dose of Lenvatinib mesylate and (ii) sodium bicarbonate in a range of from 20 to 55%, by weight based on the total weight of the composition, wherein the weight ratio of Lenvatinib mesylate to sodium bicarbonate ranges from 1:1.5 to 1:5.

2. The pharmaceutical composition according to claim 1, wherein the weight ratio of Lenvatinib mesylate to sodium bicarbonate ranges from 1:2 to 1:4.

3. The pharmaceutical composition according to claim 1, wherein the composition further comprises:
   a) at least one diluent in an amount of from 15% to 75% by weight based on the total weight of the composition;
   b) optionally, disintegrant in an amount of from 1% to 25% by weight based on the total weight of the composition; and
   c) lubricant in an amount of from 1 to 5% by weight based on the total weight of the composition.

4. The pharmaceutical composition according to claim 3, wherein the diluent is present in an amount of from 35% to 65% by weight based on the total weight of the composition.

5. The pharmaceutical composition according to claim 3, wherein the diluent is MCC, mannitol or a mixture of both.

6. A pharmaceutical composition according to claim 1, comprising, based on the total weight of the composition,
   a) a therapeutically effective dose of lenvatinib mesylate in an amount of from 4% to 25% by weight;
   b) microcrystalline cellulose in an amount of from 20% to 65% by weight;
   c) sodium bicarbonate in an amount of from 20 to 50%;
   d) optionally, low substituted hydroxypropyl cellulose in an amount of from 15% to 25% by weight;
   e) mannitol in an amount of from 7% to 18% by weight; and
   f) talc in an amount of from 1% to 5% by weight.

7. The pharmaceutical composition according to claim 1 that is prepared by wet granulation.

8. The pharmaceutical composition according to claim 1 that is prepared by direct mix.

9. A pharmaceutical composition according to claim 6 prepared by wet-granulation, which process comprises:
   a) mixing Lenvatinib mesylate and sodium bicarbonate wherein the weight ratio of Lenvatinib mesylate to sodium bicarbonate ranges from 1:1.5 to 1:5;
   b) adding one or more pharmaceutically acceptable excipients to form a mixture;
   c) wet-granulating the resulting mixture to form a granulate;
   d) further mixing the obtained granulate with one or more further pharmaceutically acceptable excipients to form a further mixture; and
   e) optionally encapsulating the granules.

10. The pharmaceutical composition according to claim 6, wherein the therapeutically effective dose of lenvatinib free base is 4 mg, 10 mg or 24 mg.

11. The pharmaceutical composition according to claim 1 in the form of a capsule.

12. The pharmaceutical composition according to claim 3, wherein said diluent is present in an amount of from 30% to 70% by weight, based on the total weight of the composition.

13. The pharmaceutical composition according to claim 6, wherein said mannitol is present in an amount of 5% to 10% by weight.

14. The pharmaceutical composition according to claim 11, wherein said composition has an in vitro dissolution profile wherein at least 85% of the Lenvatinib mesylate is released at fifteen minutes, wherein the dissolution profile is measured in a dissolution study in 900 ml HCl 0.1N (pH 1) using a USP apparatus II at 50 rpm at 37° C.

15. A pharmaceutical composition, comprising, based on the total weight of the composition,
   g) a therapeutically effective dose of lenvatinib mesylate in an amount of from 4% to 25% by weight;
   h) microcrystalline cellulose in an amount of from 20% to 65% by weight;
   i) sodium bicarbonate in an amount of from 20 to 55%;
   j) optionally, low substituted hydroxypropyl cellulose in an amount of from 15% to 25% by weight;
   k) mannitol in an amount of from 7% to 18% by weight; and
   l) Talc in an amount of from 1% to 5% by weight; wherein the weight ratio of Lenvatinib mesylate to sodium bicarbonate ranges from 1:1.5 to 1:5.

16. The pharmaceutical composition according to claim 15, wherein the therapeutically effective dose of lenvatinib free base is 4 mg, 10 mg or 24 mg.

17. The pharmaceutical composition according to claim 16 in the form of a capsule.

\* \* \* \* \*